(12) United States Patent
Jagelski et al.

(10) Patent No.: US 10,993,719 B2
(45) Date of Patent: May 4, 2021

(54) REINFORCED MECHANICAL HEMOSTASIS CLIP

(71) Applicant: BOSTON SCIENTIFIC SCIMED, INC., Maple Grove, MN (US)

(72) Inventors: Matthew R. Jagelski, Marlborough, MA (US); Greg Trumbull, Littleton, MA (US); Ryan Evers, Billerica, MA (US); Kevin John Wilcox, Brighton, MA (US); Caitlyn Bintz Ashton, Marlborough, MA (US); Heather Larson, Sudbury, MA (US); Shawn Ryan, Littleton, MA (US); Dennis Hubbard, Lancaster, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 148 days.

(21) Appl. No.: 16/129,330

(22) Filed: Sep. 12, 2018

(65) Prior Publication Data

US 2019/0105046 A1    Apr. 11, 2019

Related U.S. Application Data

(60) Provisional application No. 62/570,905, filed on Oct. 11, 2017.

(51) Int. Cl.
*A61B 17/08* (2006.01)
*A61B 17/00* (2006.01)
(Continued)

(52) U.S. Cl.
CPC ........ *A61B 17/083* (2013.01); *A61B 17/0057* (2013.01); *A61B 17/122* (2013.01);
(Continued)

(58) Field of Classification Search
CPC .... A61B 2017/086; A61B 2017/00584; A61B 2017/0488; A61B 17/086; A61B 17/0487; A61B 17/128; A61B 17/1285
See application file for complete search history.

(56) References Cited

U.S. PATENT DOCUMENTS

2002/0173805 A1    11/2002  Matsuno et al.
2003/0083677 A1     5/2003  Damarati
(Continued)

FOREIGN PATENT DOCUMENTS

WO        2015179396        11/2015

*Primary Examiner* — Wade Miles
*Assistant Examiner* — Mohammed S Adam
(74) *Attorney, Agent, or Firm* — Fay Kaplun & Marcin, LLP (57) ABSTRACT

A device for treating a tissue includes a capsule extending longitudinally from a proximal end to a distal end and including a channel extending therethrough, clip arms, proximal ends of which are slidably received within the channel of the capsule so that the clip arms are movable between an open configuration, in which distal ends of the clip arms extend distally past the distal end of the capsule to be separated from one another, and a closed configuration, in which the clip arms are restrained via an interior surface of the capsule so that distal ends of the clips arms are drawn toward one another, and a reinforcement element coupled to the clip arms, the reinforcement element preventing deflection of the clip arms when engaging a target tissue.

3 Claims, 11 Drawing Sheets

(51) Int. Cl.
*A61B 17/122* (2006.01)
*A61B 17/06* (2006.01)
*A61B 17/12* (2006.01)
*A61B 17/064* (2006.01)
*A61B 17/068* (2006.01)

(52) U.S. Cl.
CPC ........ *A61B 17/1227* (2013.01); *A61B 17/068* (2013.01); *A61B 17/06166* (2013.01); *A61B 2017/00584* (2013.01); *A61B 2017/00668* (2013.01); *A61B 2017/0641* (2013.01); *A61B 2017/12004* (2013.01)

(56) References Cited

U.S. PATENT DOCUMENTS

| | | |
|---|---|---|
| 2007/0213747 A1* | 9/2007 | Monassevitch .... A61B 17/0643 606/151 |
| 2010/0280533 A1 | 11/2010 | Martinez et al. |
| 2012/0116419 A1 | 5/2012 | Sigmon, Jr. |
| 2012/0142597 A1 | 6/2012 | Garcia et al. |
| 2014/0142597 A1 | 5/2014 | Winkler et al. |
| 2016/0354101 A1 | 12/2016 | Melsheimer |

\* cited by examiner

REINFORCED MECHANICAL HEMOSTASIS CLIP

PRIORITY CLAIM

This present disclosure claims priority to U.S. Provisional Patent Application Ser. No. 62/570,905 filed Oct. 11, 2017; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating or damaging the wall of the GI tract, or may require closure of the GI tract wall as part of the procedure. Endoscopic closure reduces cost and may reduce the trauma and inconvenience associated with these procedures. However, conventional tissue closure devices may be insufficient to close/capture large volumes of tissue. A reinforced clip opening would allow more tissue to be clipped and treated for larger tissue issues.

SUMMARY

The present disclosure relates to a device for treating a tissue. The device includes a capsule extending longitudinally from a proximal end to a distal end and including a channel extending therethrough, clip arms, proximal ends of which are slidably received within the channel of the capsule so that the clip arms are movable between an open configuration, in which distal ends of the clip arms extend distally past the distal end of the capsule to be separated from one another, and a closed configuration, in which the clip arms are restrained via an interior surface of the capsule so that distal ends of the clips arms are drawn toward one another and a reinforcement element coupled to the clip arms, the reinforcement element preventing deflection of the clip arms when engaging a target tissue.

In an embodiment, the reinforcement element is a suture, first and second end portions of the suture being fixed to an interior surface of each of the clip arms so a length of the suture extends between the clip arms.

In an embodiment, each of the clip arms include first and second holes extending therethrough, the first end portion of the suture extending through the first and second holes of a first clip arm and the second end portion of the suture extending through the first and second holes of a second clip arm, first and second ends of the suture each including an increased diameter element having a diameter larger than a diameter of the first and second holes to prevent the suture from being pulled through the first and second holes, wherein the increased diameter elements are positioned at an interior surface of the clip arms.

In an embodiment, the clip arms include first and second flanges extending from lateral sides of the clip arms, the first and second winged flanges configured to be folded toward a longitudinal axis of the clip arms to an interior surface thereof to secure ends of the suture to the clip arms.

In an embodiment, the reinforcement element includes first and second sutures, the first and second sutures extending from distal ends coupled to first and second clip arms, respectively, to proximal ends coupled to a central member within the capsule channel, wherein the proximal end of the first suture is coupled to a lateral side of the central member closest to the second clip arm and the proximal end of the second suture is coupled to a lateral side of the central member closest to the first clip arm so that the first and second sutures form a crisscross.

In an embodiment, proximal portions of the first and second sutures pass through the central member to form the crisscross therein.

In an embodiment, the device further comprises a second suture including first and second ends coupled to a central member within the capsule channel, a medial portion of the second suture wrapping around a medial portion of the first suture.

In an embodiment, the reinforcement element comprises first and second support members, the first and second support members extending from distal ends coupled to an outer surface of the first and second clip arms, respectively, to proximal ends coupled to opposing lateral sides of the capsule.

In an embodiment, each of the distal ends of the first and second support members is coupled to the clip arms via a pivot joint.

In an embodiment, each of the proximal ends of the first and second support member is coupled to the capsule via a sliding joint, the sliding joint allowing the proximal ends of the support members to move proximally and distally along an axis parallel to the central longitudinal axis of the capsule.

In an embodiment, the sliding joint also permits rotational movement of the proximal ends of support members.

In an embodiment, the reinforcement element includes at least one rib extending longitudinally along an outer surface of a flexing portion of the clip arms.

The present disclosure also relates to a clipping device. The device includes a proximal portion, a distal portion releasably coupled to the proximal portion so that the distal portion is deployable therefrom, the distal portion including a capsule extending longitudinally from a proximal end to a distal end and including a channel extending therethrough, clip arms extending from proximal ends slidably received within the channel of the capsule so that the clip arms are movable between an open configuration, in which distal ends thereof extend distally past the distal end of the capsule to be separated from one another, and a close configuration, in which the clip arms are restrained via an interior surface of the capsule so that the distal ends thereof are drawn toward one another, and at least one leaf spring extending from a proximal end to a distal end and sized and shaped to fit along an outer surface of a flexing medial portion of a clip arm, the leaf spring producing a counter force on the clip arm as it contacts target tissue to reduce deflection in the clip arm.

In an embodiment, one of the proximal and distal ends of the at least one leaf spring is fixed to the outer surface of the clip arm while the other end remains unfixed.

In an embodiment, the at least one leaf spring is coupled to the clip arm via interlocking features, the interlocking features configured to interact with mating features on the clip arms.

The present disclosure also relates to a method for treating target tissue. The method includes inserting a distal portion of a clipping device to a target area within a living body, the distal portion including a capsule and clip arms slidably received within the capsule to be movable between an open configuration, in which distal ends of the clip arms are separated from one another, and a closed configuration, in which the distal ends of the clip arms are drawn toward one another, the distal portion including a reinforcement element coupled to the clip arms, the reinforcement element preventing deflection of the clip arms when engaging a target tissue, positioning the clip arms in contact with a target tissue and clipping a target portion of tissue by positioning the target portion of tissue between the clip arms in the open configuration and drawing the clip arms toward the closed configuration to grip the target portion of tissue.

In an embodiment, the reinforcement element is a suture, first and second end portions of the suture being fixed to an interior surface of each of the clip arms so a length of the suture extends between the clip arms.

In an embodiment, the reinforcement element comprises at least one leaf spring extending from a proximal end to a distal end and sized and shaped to fit along an outer surface of a flexing medial portion of a clip arm, the leaf spring producing a counter force on the clip arm as it contacts target tissue to reduce deflection in the clip arm In an embodiment, the reinforcement element comprises first and second support members, the first and second support members extending from distal ends coupled to an outer surface of the first and second clip arms, respectively, to proximal ends coupled to opposing lateral sides of the capsule.

In an embodiment, the reinforcement element comprises first and second sutures, the first and second sutures extending from distal ends coupled to first and second clip arms, respectively, to proximal ends coupled to a central member within the capsule channel, wherein the proximal end of the first suture is coupled to a lateral side of the central member closest to the second clip arm and the proximal end of the second suture is coupled to a lateral side of the central member closest to the first clip arm so that the first and second sutures form a crisscross.

BRIEF DESCRIPTION

DETAILED DESCRIPTION

The present disclosure may be further understood with reference to the following description and the appended drawings, wherein like elements are referred to with the same reference numerals. The present disclosure is directed to an endoscopic clipping device for treating tissue perforations, defects and/or bleeds. Exemplary embodiments of the present disclosure describe a hemostatic clip having a reinforced arm opening including support mechanisms for grasping larger volumes of tissue. In particular, exemplary embodiments describe a hemostatic clip with clip arms reinforced with sutures, cables or leaf springs to resist deformation of the clip arms and allow grabbing of an increased volume of tissue. It should be noted that the terms "proximal" and "distal," as used herein, are intended to refer to toward (proximal) and away from (distal) a user of the device.

Figure 1:
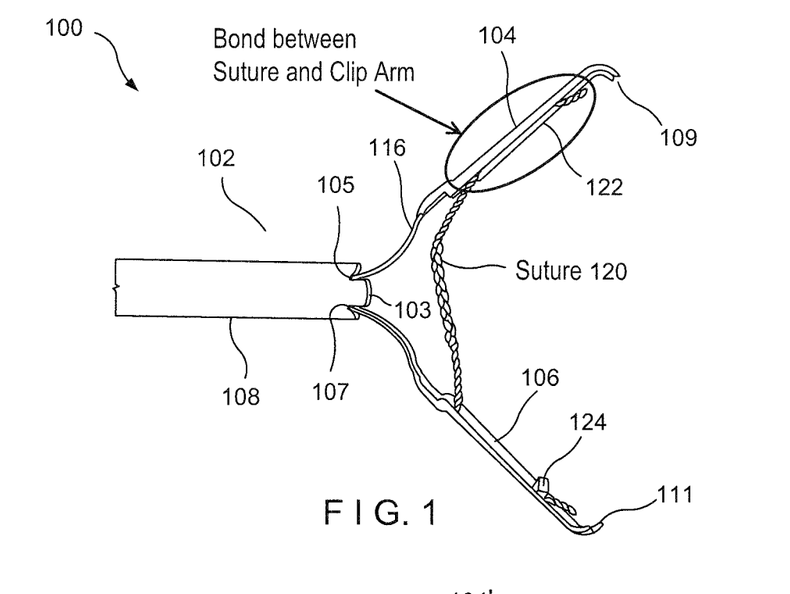
FIG. 1 is a plan view of a reinforced clip device according to a first exemplary embodiment of the present disclosure.

As shown in FIG. 1, a clip device 100 according to an exemplary embodiment of the present disclosure comprises a distal portion 102 insertable into a living body through, for example, a working channel of an endoscope to target tissue to be treated. The device 100 is sufficiently flexible to permit it to traverse a tortuous path through the body—e.g., passing through the working channel of an endoscope inserted through a natural body lumen accessed via a natural bodily orifice. The distal portion 102 includes first and second clip arms 104, 106 slidably received within a longitudinal channel 103 of a capsule 108. The first and second clip arms 104,106 can be moved between an open configuration, in which the distal ends 109, 111 of the clip arms 104,106 are separated from one another to receive target tissue therebetween, and a closed configuration, in which the distal ends 109, 111 of the clip arms 104, 106 are moved toward one another to grip the target tissue therebetween. The distal portion 102 is releasably coupled to a proximal portion (not shown) of the device 100, which includes a handle (not shown) that remains outside the body accessible to a user as the distal portion 102 is deployed. The clip arms 104, 106 are movable between the open and the closed configurations via a control member (not shown) extending into the capsule 108. A proximal end (not shown) of the control member (not shown) is connected to an actuator on the handle. In this embodiment, a distal end (not shown) of the control member (not shown) is coupled to proximal ends 105, 107 of the clip arms 104, 106.

As further shown in FIG. 1, device 100 includes clip arms 104, 106 according to an exemplary embodiment of the present disclosure which extend from proximal ends 105, 107, respectively, to the distal ends 109, 111, with a medial curved portion 116. As those skilled in the art will understand, arms 104, 106 of this embodiment are biased toward an open tissue receiving position in which the distal ends 109, 111 are separated from one another to receive tissue. That is, the arms 104, 106 are formed so that they spring open to the tissue receiving position when they are moved distally out of the constraint of the capsule 108. However, as would be understood by those skilled in the art, the device 100 may include a separate member urging the arms 104, 106 away from one another in addition, or as an alternative, to this bias. In an exemplary embodiment, the clip arms 104, 106 may include locking tabs (not shown) at their proximal ends 105, 107 for engaging distal components (not shown) within the capsule 108 before the clip has been deployed. Locking tabs (not shown) may also form a mechanical lock with windows (not shown) formed on lateral sides of the capsule 108 after the clip has been deployed. However, those skilled in the art will understand that any of the various known mechanisms for releasably coupling a clip assembly (e.g., a capsule including clip arms) to an insertion device may be employed without deviating from the scope of the invention. As indicated above, the clip arms 104, 106 are biased toward the open configuration so that, when the clip arms 104, 106 are moved distally past a distal end 116 of the capsule 108, distal ends 109, 111 of the clip arms 104,106 separate from one another to the open configuration. When the clip arms 104, 106 are drawn proximally into the capsule 108, contact with the capsule 108 draws the clip arms 104, 106 toward one another to the closed configuration. Upon deployment, the clip arms 104, 106 are locked within the capsule 108 which holds them in the closed position as would be understood by those skilled in the art. As described above, the clip arms 104, 106 are moved between the open and closed configurations via the control member (not shown), which is moved proximally and distally relative to the capsule 108 via an actuator at a handle that remains outside the body. In an exemplary embodiment, the clip arms 104, 106 may include an increased opening width. For example, the clip arms 104, 106 may have an arm-tip to arm-tip opening between 15 and 20 millimeters (mm) and, more particularly, between 16 and 18 millimeters. In another embodiment, the clip arms 104, 106 according to this embodiment may also have a length of between 2 and 3 mm greater than current clip arms. Specifically, the clip arms 104, 106 may be between 6 and 8 mm and, more particularly, a length of 7.5 mm. However, it will be understood by those skilled in the art that the clip arms 104, 106 may have any length or arm tip-to-arm tip opening. The clip arms 104, 106 according to this embodiment are interconnected by a suture 120 tethered thereto to create a truss system to support increased tissue acquisition by distributing the force between the clip and the target tissue. For example, as can be seen in FIG. 1, end portions 122, 124 of the suture 120 are bonded to the interior of each of the clip arms 104, 106. The suture 120, in this embodiment, is bonded to the clip arms 104, 106 using, for example, an epoxy. However, it will be understood that the suture 120 may be coupled or bonded to the clip arms 104, 106 by any known method. The length of the suture 120 may vary depending on the size of the clip and the width of the opening between the clip arms 104, 106. For example, a wide clip may require a suture 120 with a longer length than is required for a smaller clip. The suture 120 may be formed of any suitable material such as, for example, a stranded polyester suture with a 0.008 diameter.

Figure 2:
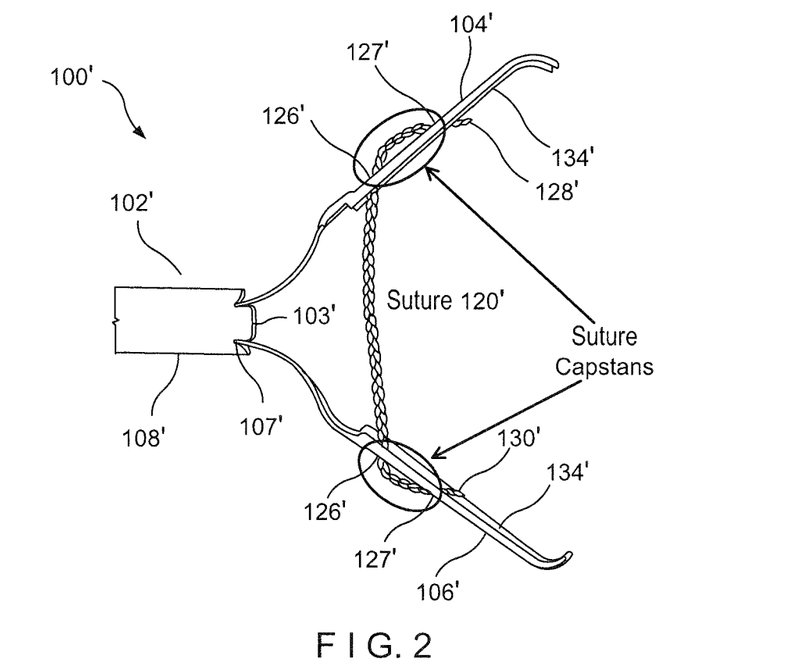
FIG. 2 is a plan view of a reinforced clip device of FIG. 1 according to a second exemplary embodiment.
Figure 3:
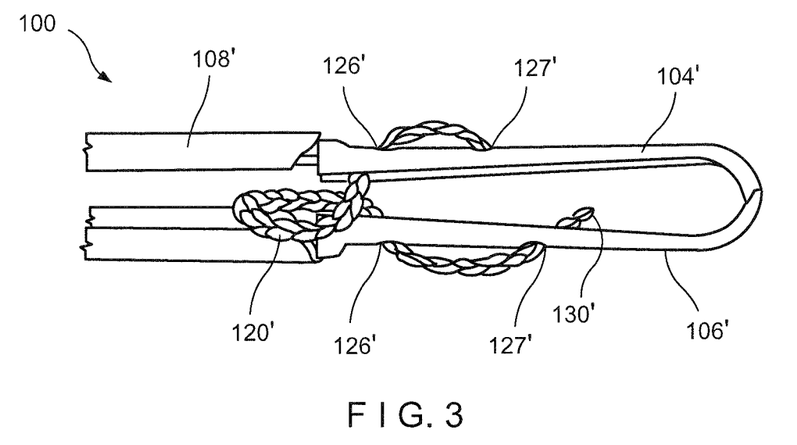
FIG. 3 is a plan view of the clip device of FIG. 2 in the retracted position.
Figure 4:
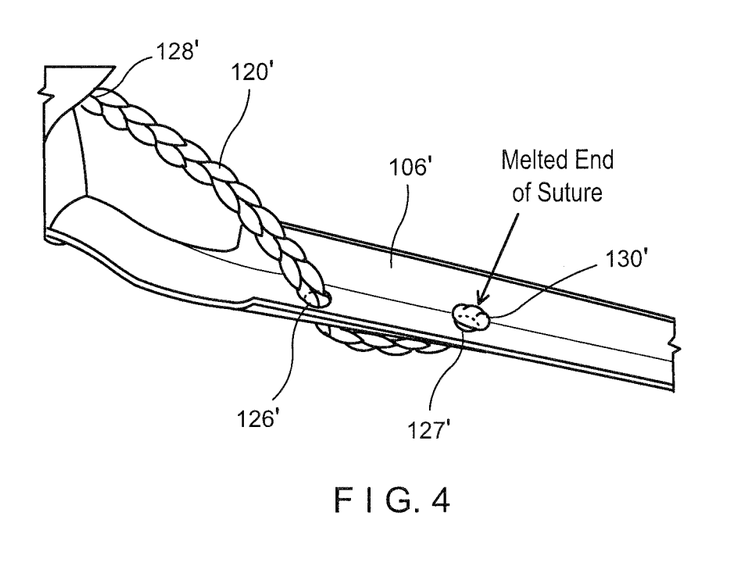
FIG. 4 is a perspective view of a clip arm of the clip device of FIG. 2 according to first exemplary embodiment of the present disclosure.
Figure 5:
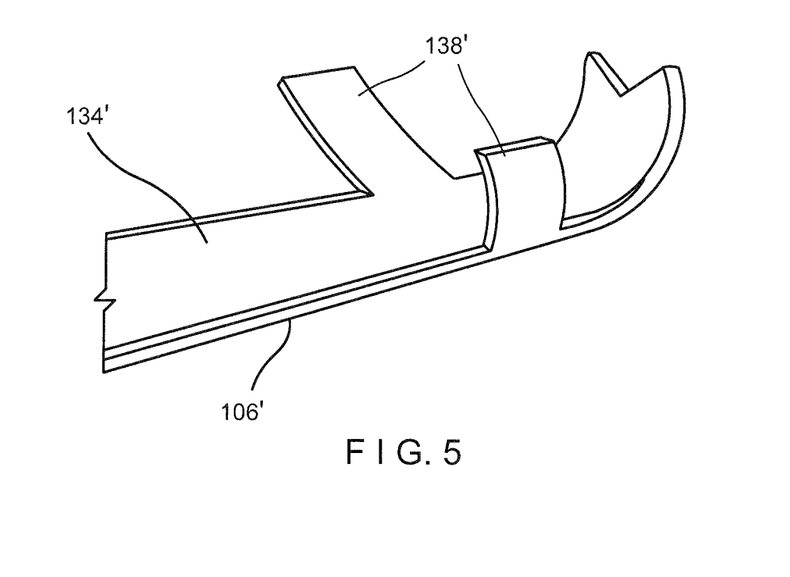
FIG. 5 is a perspective view of the clip arm of the clip device of FIG. 2 according to a second exemplary embodiment of the present disclosure.
Figure 6:
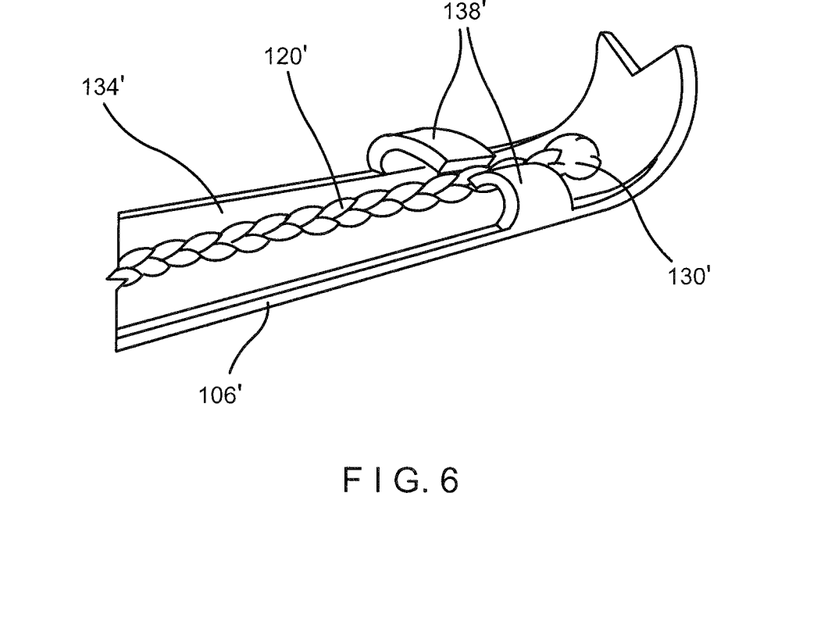
FIG. 6 is another perspective view of the clip arm of FIG. 5.

As shown in FIG. 2, a device 100' according to an alternate embodiment is substantially similar to the device 100 comprising distal portion 102' including clip arms 104', 106' slidably received within a capsule 108' to be moved between an open configuration and a closed configuration via a control member (not shown). According to this embodiment, the suture 120' is joined to the clip arms 104', 106' via one or more hole features 126', 127' in the clip arms 104', 106' through which the suture 120' passes. In this embodiment, each end 128', 130' of the suture 120' is passed from the inside of the clip arm 104', 106' to the outside of the clip arm 104', 106' through a first proximal hole 126' and then passed back to the inside of the clip arm 104', 106' through a second distal hole 127' to form a capstan. This capstan configuration prevents the suture 120' from pulling out of the holes 126', 127' and keeps the ends 128', 130' of the suture on the internal surface 134' of the clip arms 104', 106'. Furthermore, having the ends 128', 130' of the suture 120' joined to the internal surface 134 of the clip arms 104, 106 minimizes the possibility of damage to the suture 120' and reduces the risk that the suture 120' will be caught as passes through the working channel of the endoscope. The remaining portion of the suture 120' that bridges the clip arms 104, 106 naturally folds on itself and falls beside the capsule 108' as shown in FIG. 3. In an embodiment, the ends 128', 130' of the suture 120' are knotted or melted to form a ball with a diameter greater than that of the holes 126', 127', preventing the ends 128', 130' from being pulled through the holes 126', 127'. In another embodiment, the suture ends 128', 130' are crimped by adding crimp features 136' to the clip arms 104', 106'. The crimp features 136' include first and second flanges 138', which may be folded toward the interior surface 134' of the clip arms 104', 106'. When folded, the flanges 138' contact and secure the suture ends 128', 130' to the interior surface 134', preventing them from pulling through the holes 126', 127'.

Figure 7:
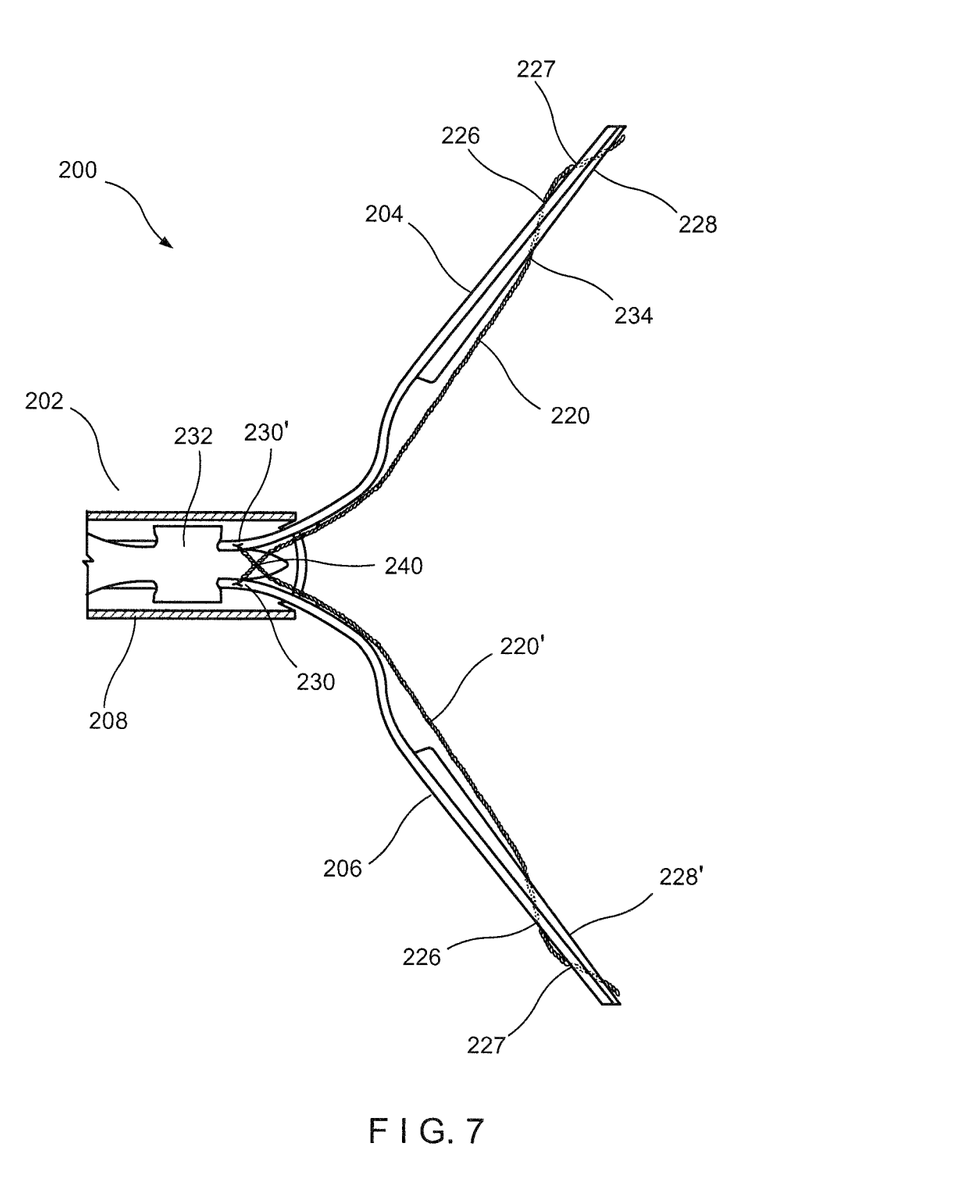
FIG. 7 is a plan view of a reinforced clip device according to a third exemplary embodiment of the present disclosure.

As shown in FIG. 7, a device 200 according to an alternate embodiment is substantially similar to the device 100' comprising distal clip portion 202 including clip arms 204, 206 slidably received within a capsule 208 so that the clip arms 204, 206 may be moved between an open configuration and a closed configuration via a control member (not shown) as described above. However, according to this embodiment two sutures 220, 220' are employed. A first suture 220 is attached to the first clip arm 204 at a distal end 228 and attached to a central member 232 within the capsule 208 at the proximal end 230. Similarly, a second suture 220' is attached to the second clip arm 206 at the distal end 228' and attached to the central member 232 at the proximal end 230'. The proximal ends 230, 230' of the sutures 220, 220' are attached to opposing sides of the central member 232 to form a crisscross 240 through the central member 232. For example, the proximal end 230 of the first suture 220 is attached to the lateral side of the central member 232 closest to the second arm 206 while the proximal end 230' of the second suture 220' is attached to the lateral side of the central member 232 closest to the first arm 204. Thus, because each of the sutures 220, 220' is attached to a single one of the clip arms 204, 206, the load applied to one clip arm will not influence that applied to the opposite clip arm. As would be understood by those skilled in the art, the sutures 220, 220' may be attached to the arms 204, 206 in any suitable manner, such as the attachments described in regard to the device 100'. For example, the distal ends 228, 228' of the sutures 220, 220' are passed from the inside of the clip arm to the outside of the clip arm through a first hole 226 and then passed back to the inside of the clip arm through a second hole 227 to form a capstan. In an embodiment, the distal ends 230, 230' of the sutures 204, 206 may be knotted or melted so that the ends 230, 230' form a ball with a greater diameter that the holes 226, 227, preventing the distal ends 230, 230' from being pulled through the holes 226, 227. In another embodiment, the suture distal ends 230, 230' may be crimped by adding crimp features 236 to the clip arms 204, 206. Crimp features 236 include flanges 238, which may be folded toward the interior surface 234 of the clip arms 204, 206. When folded, the flanges 238 contact and secure the suture ends 220, 220' to the interior surface 234, preventing them from pulling through the holes 226, 227.

Figure 8:
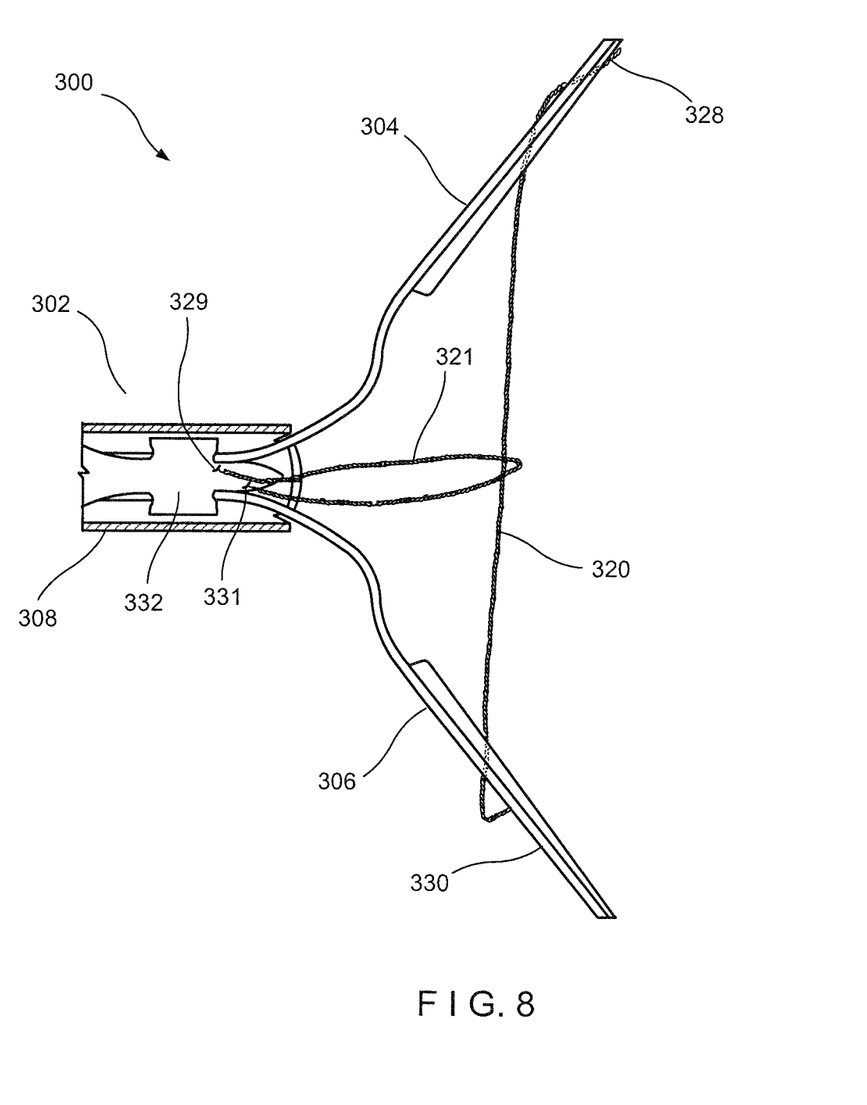
FIG. 8 is a plan view of a reinforced clip device according to a fourth exemplary embodiment of the present disclosure.

As shown in FIG. 8, a device 300 according to an alternate embodiment is substantially similar to the device 100' comprising a distal clip portion 302 including clip arms 304, 306 slidably received within a capsule 308 so that they may be moved between an open configuration and a closed configuration via a control member (not shown) as described above. In this embodiment, a first suture 320 is connected at a first end 328 to the arm 304 and at its second end 330 to the arm 306 substantially similarly to clip device 100. Thus, a length of the first suture 320 limits a maximum deflection in the clip arms 304, 306 in the same manner as described with regards to device 100'. However, to control the excess length of the first suture 320 when the device is in the closed configuration, a second suture 321 is looped about the first suture 320 and extends through a central member anchor 332. Specifically, a first end 329 of the second suture 321 is coupled to the central member 332 and a medial portion of the suture 321 is looped around the medial portion of the first suture 320 extending between the arms 304, 306 so that the second end 331 of the second suture 321 is also coupled to the central member 332. The second suture 321 may have an elasticity similar to or less than the elasticity of the first suture 320. Thus, as the central anchor 332 is drawn proximally into the capsule 308 as the clip arms 304, 306 are drawn proximally into the capsule 308 to the closed configuration, the excess length of the first suture 320 is pulled into the capsule 308 through the distal opening thereof by the second suture 321.

Figure 9:
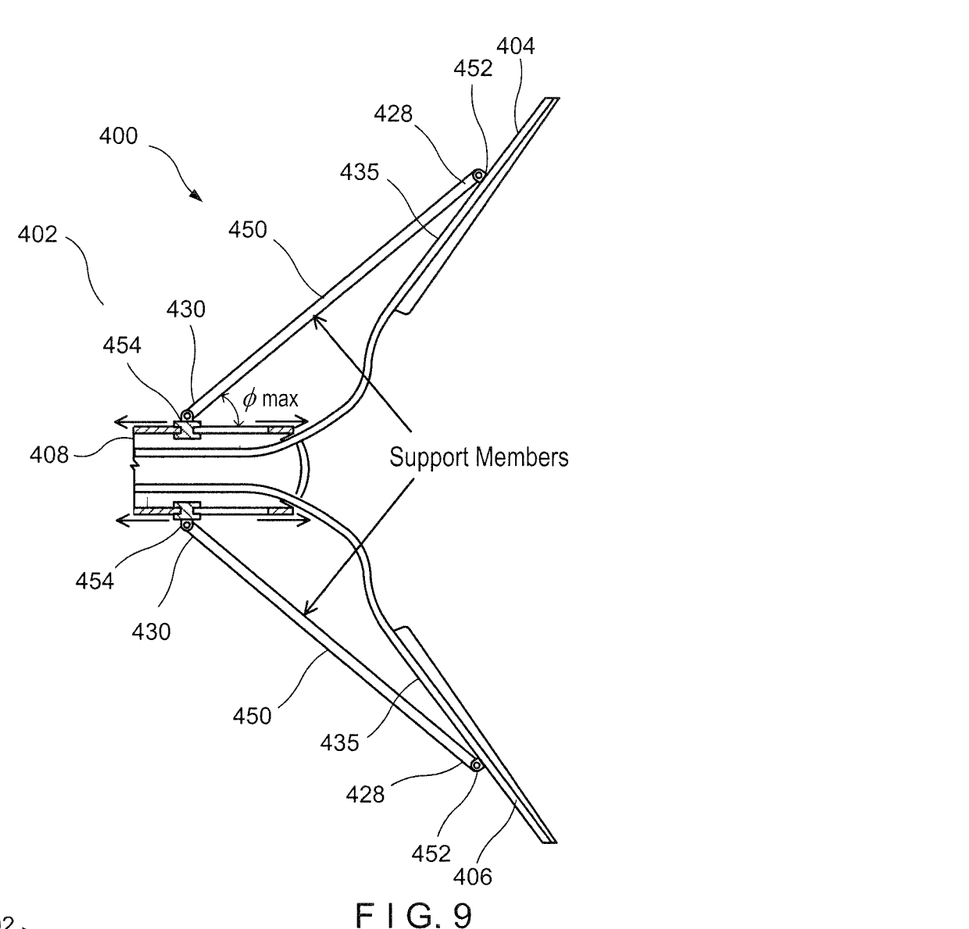
FIG. 9 is a plan view of a reinforced clip device according to a fifth exemplary embodiment of the present disclosure.
Figure 10:
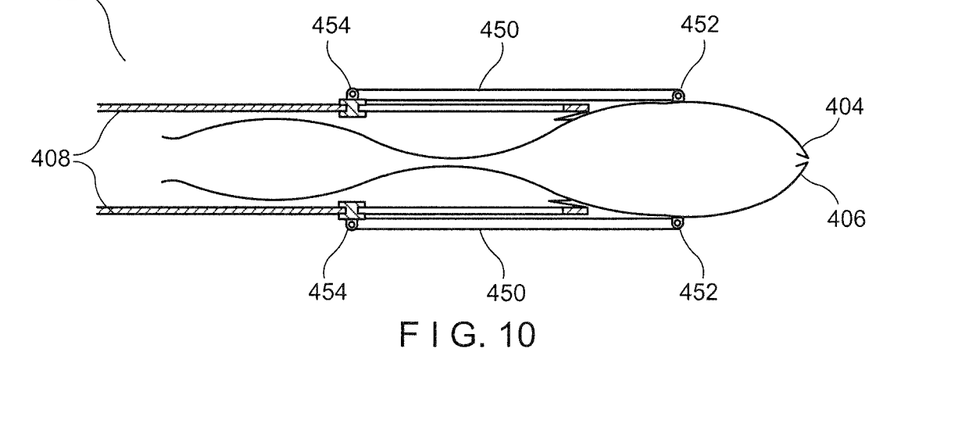
FIG. 10 is a plan view of the clip device of FIG. 9 in the retracted position.
Figure 11:
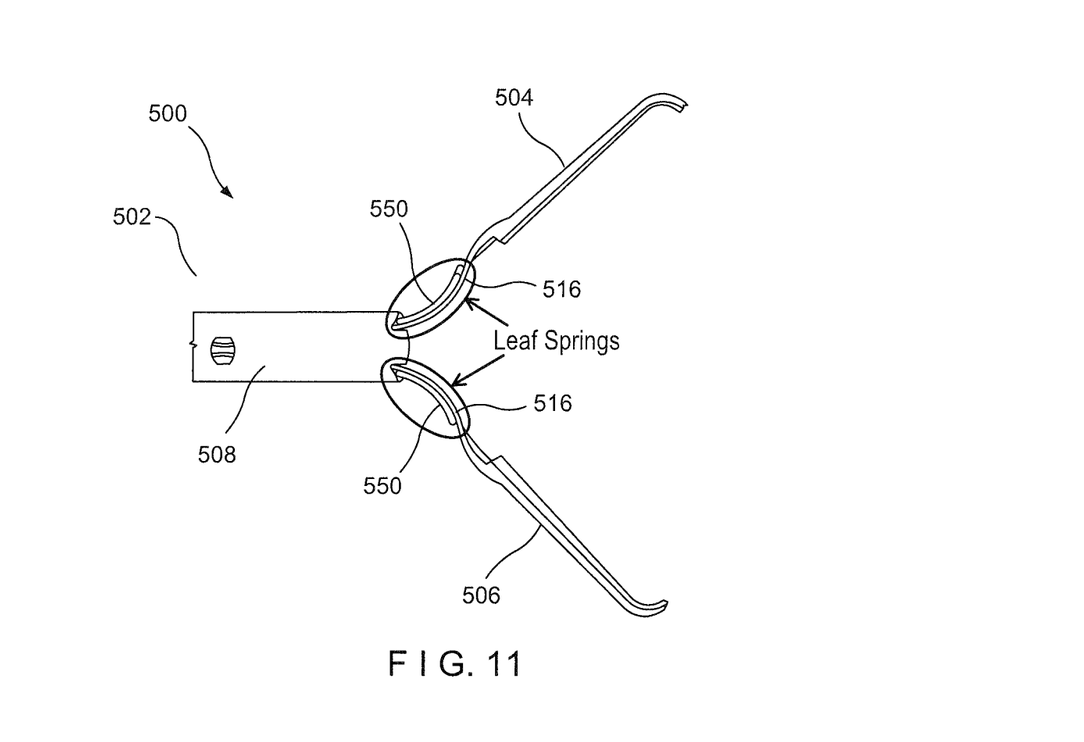
FIG. 11 is a plan view of a reinforced clip device according to a sixth exemplary embodiment of the present disclosure.
Figure 12:
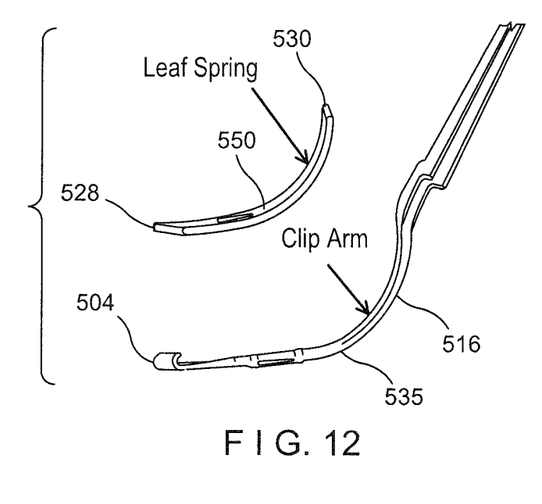
FIG. 12 is a plan view of the clip arm and leaf spring of the clip device of FIG. 11.
Figure 13:
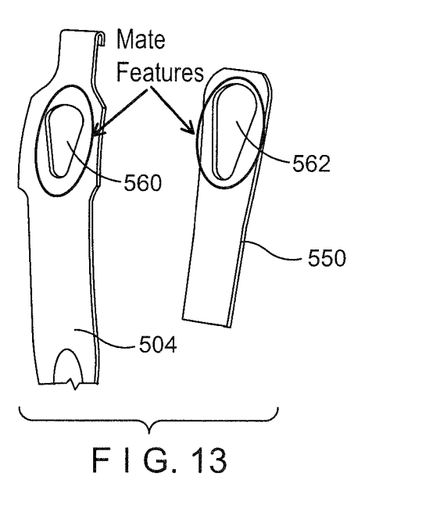
FIG. 13 is a perspective view of the pin receiving feature and hole of the clip device of FIG. 11.

As shown in FIGS. 9-10, a device 400 according to an alternate embodiment is substantially similar to the device 100' comprising distal clip portion 402 including clip arms 404, 406 slidably received within a capsule 408 to be moved between an open configuration and a closed configuration via a control member (not shown) as described above. However, in this embodiment, support members 450 are used to control the maximum deflection of the clip arms 404, 406. Each of the support members 450 extends from a proximal end 430 attached to an outer surface of the capsule 408 to a distal end 428 pivotally attached to an outside surface 435 of a corresponding one of the clip arms 404, 406. The distal ends 428 of the support members 450, in this embodiment, are attached to the clip arms 404, 406 via a pivot joint 452, which allows for motion only rotationally. Specifically, the distal ends 428 of the support members 450 pivot about a pivot axis, P, running perpendicular to longitudinal axes of the clip arms 404, 406, as shown in FIG. 8. The distal ends 428 of the support members 450 are preferably attached to a medial portion of the clip arms 404, 406. However, it will be understood that the distal ends 428 may be attached to any portion of the clip arms 404, 406 so long as the length of the support members 450 is selected to correspond to the position of the location at which they are attached to the clip arms 404, 406 to achieve the desired limit on the maximum width of opening of the clip arms 404, 406. The proximal ends 430 of the support members 450, in this embodiment, are attached to opposing lateral sides of the capsule 408 via a joint 454 that allows for translational movement (i.e., a sliding joint) along an axis parallel to the central longitudinal axis of the capsule 408, as can be seen in FIG. 8. The sliding joint 454 allows the arms to move from an insertion position where the arms 404, 406 are positioned proximally within the capsule, as seen in FIG. 9, to the extended position of FIG. 8 where the arms 404, 406 are extended distally past the distal end of the capsule 408. The joint 454 also permits rotational movement of the support members 450 laterally in a plane including the support members 450 so that an angle formed between the support member 450 and the capsule 408 may increase or decrease as required. In this embodiment, the joint 454 includes a mechanical hard stop 456 to limit maximum rotation of the support members 450 once the clip arms 404, 406 have reached a maximum opening. The support members 450 may be composed of any suitable biocompatible material, which provides the strength necessary to prevent deflection of the clip arms such as, for example, Stainless Steel.

Figure 14:
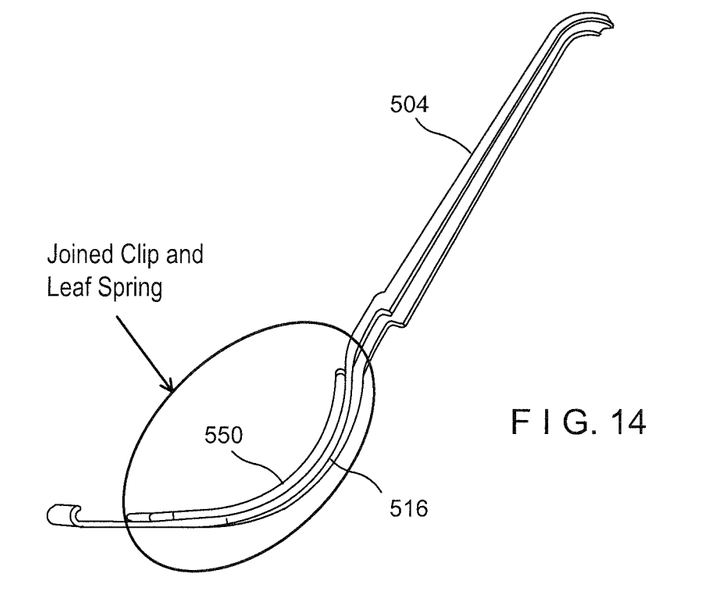
FIG. 14 is a plan view of the clip arm and leaf spring of the clip device of FIG. 11 according to another exemplary embodiment.
Figure 15:
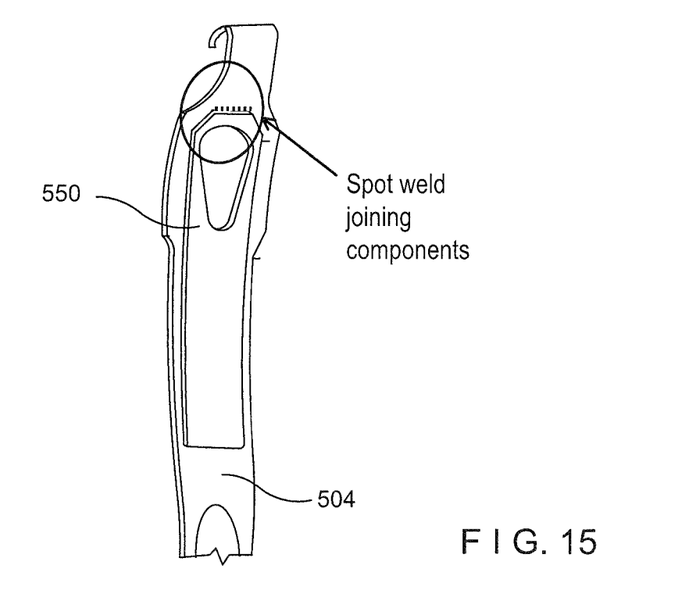
FIG. 15 is a perspective view of the clip arm and leaf spring of the device of FIG. 14.

As shown in FIGS. 11-15, a device 500 according to an alternate embodiment is substantially similar to the device 400 comprising distal clip portion 502 including clip arms 504, 506 slidably received within a capsule 508 to be moved between an open configuration and a closed configuration as described above. However, in this embodiment, leaf springs 550 are included in lieu of the support members 450 to control the maximum deflection of the clip arms 504, 506. The leaf springs 550, in this embodiment, are single leaf springs extending from a proximal end 528 to a distal end 530 along an arc. The leaf springs 550 are sized and shaped to fit along the outer surface 535 of the curved medial portion 516 of the clip arms 504, 506, with the curve of the leaf springs 550 substantially corresponding to the curve of the medial portion 516, depending on the extent of clip arm deformability that is preferred. In this embodiment, proximal ends 528 are fixed to the outer surface 535 of the clip arms 504, 506 while distal ends 530 are left free. Thus, distal ends 530 of the springs 550 are capable of sliding along the clip arms 504, 506 as the clip is deflected outward and backward. Positioning the leaf springs 550 behind the flexing medial portion 516 of the clip arms 504, 506 produces a counter force on the clip arms 504, 506 as they make contact with the target tissue, reducing the deflection in the clip arms 504, 506. In an exemplary embodiment, the leaf springs 550 are aligned with and fixed to the clip arms 504, 506 using preexisting pin receiving features 560 on the clip arms 504, 506 and using the same pin-type connection disposed in some existing clips such as, for example, the Resolution Clip™, Resolution 360 Clip™ and Resolution 360 Wide Clip™ as would be understood by those skilled in the art. For example, the leaf springs 550 may include a pin-receiving hole 562 extending therethrough sized and shaped to correspond with the pin receiving features 560 in the clip arms 504, 506. In this embodiment, the pin-receiving holes and features 560, 562 are "teardrop" shaped—i.e., substantially oval with one tapered side. Thus, the pin component within the capsule 508 extends through both the clip arm feature 560 and the leaf spring hole 562, pinning the two components together. In another exemplary embodiment, the leaf springs 550 may be joined to the clip arms 504, 506 by placing a spot weld on the proximal ends 528 of the springs 550, as shown in FIG. 14. This weld connection may facilitate handling of the device 500 during assembly. The leaf springs 550 may be composed of any biocompatible metal such as, for example, Stainless Steel. The leaf springs 550 may be formed of any thickness depending on the desired amount of counterforce to the clip arms 504, 506. In an exemplary embodiment, multiple leaf springs of equal or different thicknesses may be stacked on top of one another to achieve the desired amount of counterforce to the clip.

Figures 16, 17:
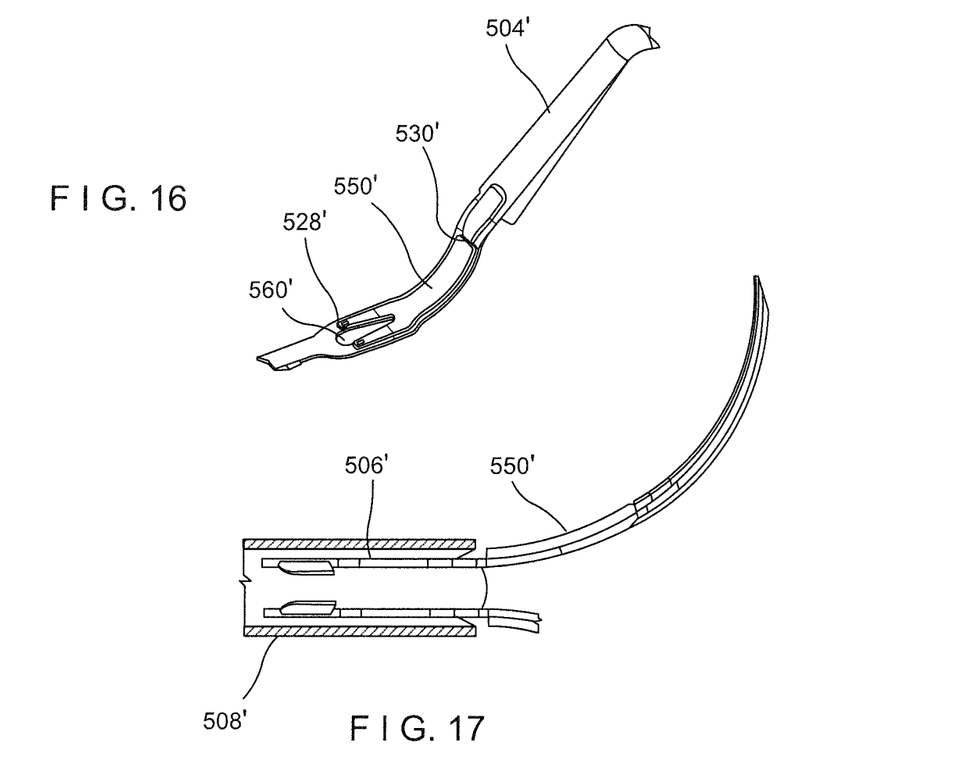
FIG. 16 is a plan view of a reinforced clip device according to a seventh exemplary embodiment of the present disclosure.
FIG. 17 is a side view of the clip device of FIG. 16.
Figure 18:
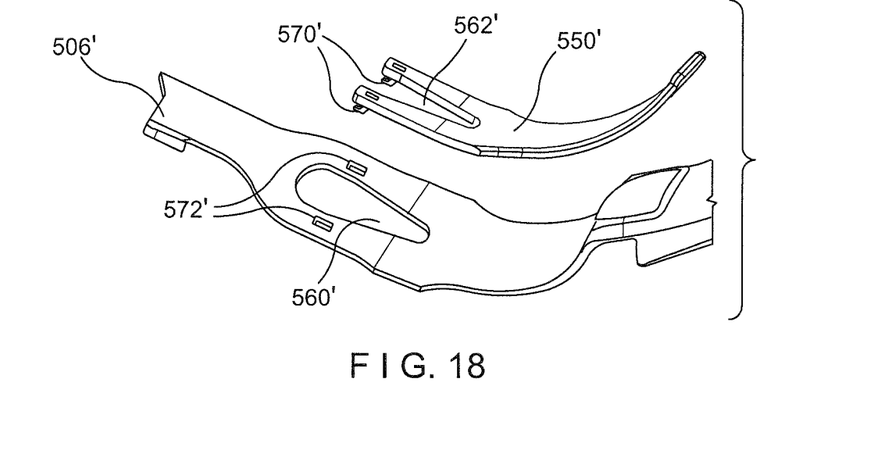
FIG. 18 is a perspective view of the leaf spring and clip arm of the device of FIG. 16.

As shown in FIGS. 15-18, a device 500' according to an alternate embodiment is substantially similar to the device 500. However, in this embodiment, the leaf springs 550' may include interlocking features 570' that improve the manufacturability of attaching leaf springs 550' to the clip arms 504', 506'. In this embodiment, the distal ends 530' of the leaf springs 50' are still free and able to slide along the outer surface of the clip arms. However, it will be understood that in another exemplary embodiment the proximal ends 528' of the leaf springs 550' may be free while the distal ends 530' are coupled to the clip arms 504', 506'. The proximal ends 528' of the leaf springs 550' are attached to the clip arms 504', 506' via interlocking features 570'—i.e., snap, hooks, detents, etc. The clip arms may include mating features 572' such as, for example, slots or grooves, that interface with the interlocking features 570' of the leaf springs 550'. In the example of FIGS. 17-18, the interlocking features 570' of the leaf springs 550' are hooks and the mating features 572' of the clip arms 504', 506' are cut-outs. When positioned on the clip arms 504', 506' the hooks are inserted through the cutout outs to hold the leaf springs 550' in place. In addition to the interlocking features 550', the leaf spring may also include the same pin-type receiving holes 562' found in the device 500 which align with the pin receiving features 560' of the clip arms 504', 506' to provide additional stability between the two components. As shown in the figure, the distal ends 530' of the leaf springs in this embodiment are free while the proximal ends 528' are coupled to the clip arms 504', 506' to minimize any impact to the clips ability to deploy securely in the capsule 508'.

Figures 19, 20:
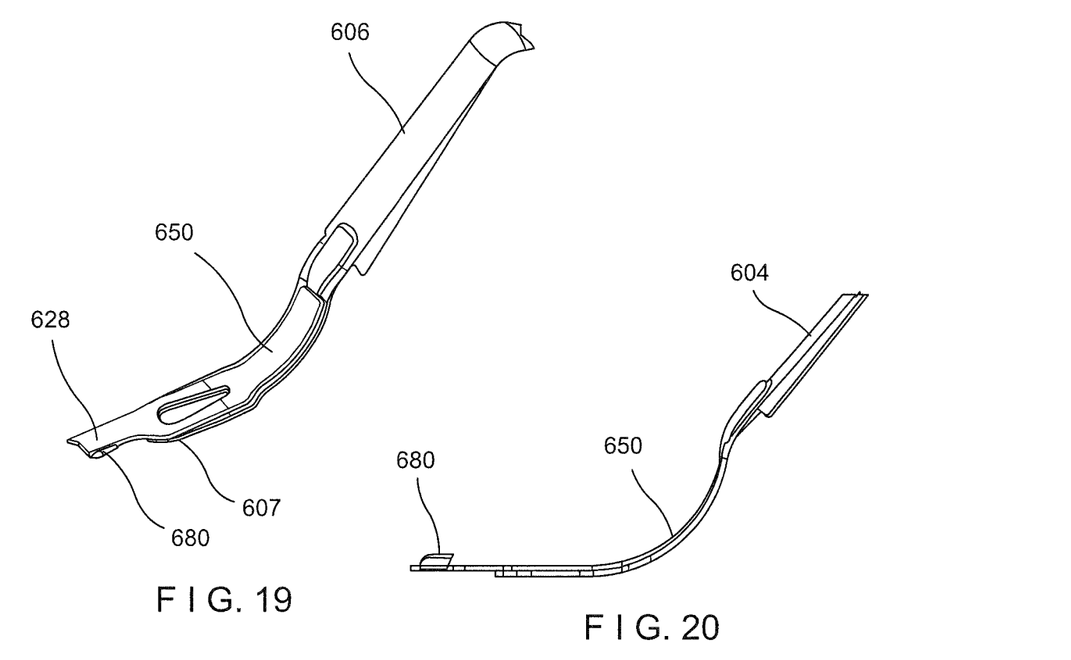
FIG. 19 is a plan view of a reinforced clip device according to a eight exemplary embodiment of the present disclosure.
FIG. 20 is a side view of the clip device of FIG. 19.
Figure 21:
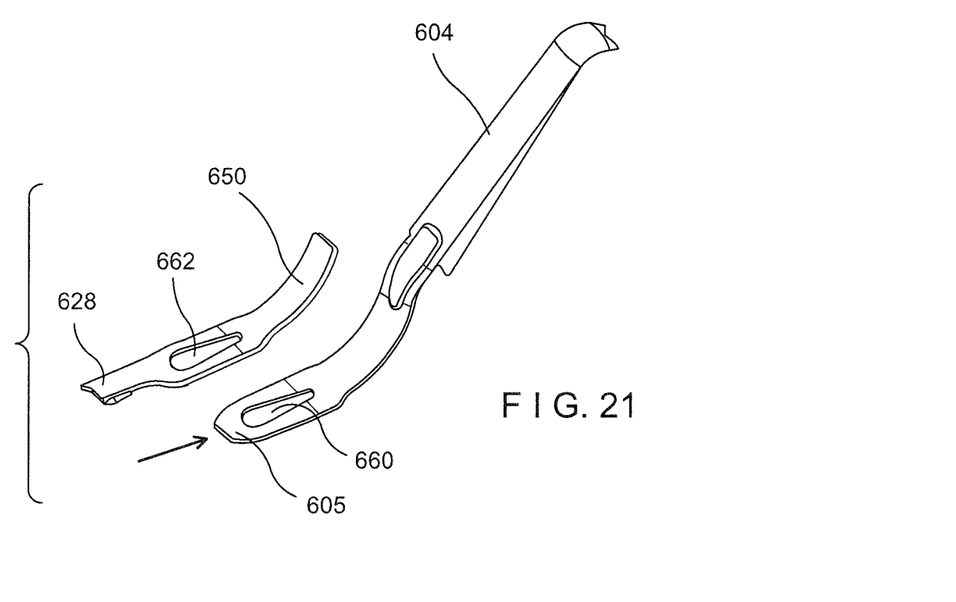
FIG. 21 is a perspective view of the leaf spring and clip arm of the device of FIG. 19.

According to an alternate embodiment, as shown in FIGS. 19-21, a device 600 is substantially similar to the device 500 describe above, comprising a pair of clip arms 604, 606 slidable within a capsule (not shown) between an open configuration and a closed configuration as described above. The device 600 includes leaf springs 650' similar to leaf springs 550, 550', which are coupled to the clip arms 604, 606. However, in this embodiment, the clip arms 604, 606 do not include locking tabs. Instead, the leaf springs 650 include locking tabs 680 at their proximal ends 628 to form a mechanical lock with windows (not shown) in the capsule (not shown) when deployed. As seen in FIG. 20, the proximal ends 628 of the leaf springs 650 extend proximally beyond the proximal ends 605, 607 of the clip arms 604, 606. Specifically, the clip arms 604, 606 of this embodiment end just proximally of the clip arm pin receiving features 660. The leaf springs 650 may include pin receiving holes 662 similar to pin receiving holes 562 to appropriately align the leaf springs 650 with the clip arms 604, 606 and aid in connection between the leaf springs 650 and the clip arms 604, 606. In an embodiment, distal ends 630 of the leaf springs 650 are coupled to the arms 604, 606 using interlocking features, which lock with mating features on the clip arms 604, 606. However, it will be understood that no further connection is necessary between the leaf springs 650 and the clip arms 604, 606 other than the pin connection through the pin receiving holes 662 and the clip arm pin receiving features 660. Specifically, an advantage of the device 600 is that the need for any additional bonding step between the leaf springs 650 and the clip arms 604, 606 is eliminated.

Figure 22:
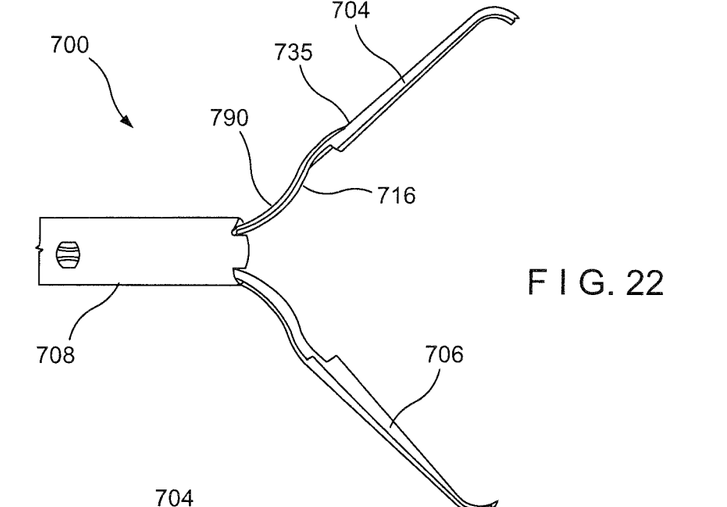
FIG. 22 is a plan view of a reinforced clip device according to a ninth exemplary embodiment of the present disclosure.
Figure 23:
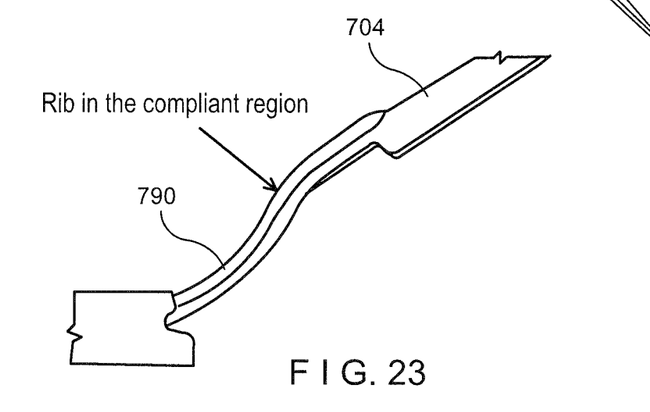
FIG. 23 is a perspective view of the clip arm of the device of FIG. 22.
Figure 24:
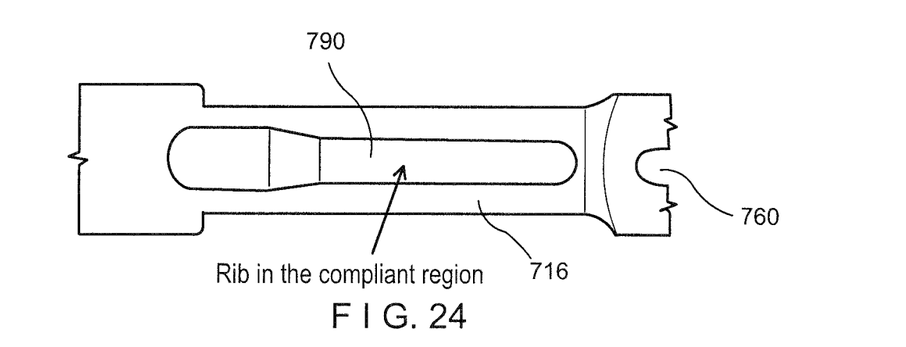
FIG. 24 is a side view of the clip arm rib feature of the device of FIG. 22.

According to an alternate embodiment, as shown in FIGS. 22-24, a device 700 is substantially similar to the device 100 describe above, comprising a pair of clip arms 704, 706 slidable within a capsule 708 between an open configuration and a closed configuration. However, in lieu of sutures, the clip arms 704, 706 may include, in an exemplary embodiment, a rib feature 790 extending longitudinally across an exterior surface 735 of one or both of the arms 704, 706. As seen in FIG. 24, the rib feature 790 extends along compliant curved portions 716 of the anus 704, 706. In this example, the rib 790 may run from just distally of the distal end of the pin-receiving feature 760, as shown in FIG. 23, to a distal end of the medial curved region 716. This rib feature 790 which may, for example, be stamped into the arms 704, 706 provides additional stiffness to the device 700 thereby reducing the deflection of the clip arms 704, 706. One advantage of this embodiment is that the change to the clip arms 706, 704 does not affect the assembly process of the device 700.

According to an exemplary method, the distal portion 102 of the device 100 may be inserted to a target area within a living body through, for example, a working channel of an endoscope. The distal portion 102 may be inserted through the working channel in the closed configuration. Once the distal portion 102 has reached the target area, the clip arms 104, 106 may be moved to the open configuration by moving the control member (not shown) distally relative to the capsule 108. As would be understood by those skilled in the art, as the clip arms 104, 106 are moved distally out of the capsule, they spring open to the open, tissue receiving configuration. The distal ends 109, 111 of the clip arms 104, 106 are positioned about the area of the tissue to be clipped, in the open configuration. The clip arms 104, 106 are then drawn proximally into the capsule (or the capsule may be advanced distally over the clip arms) to draw the clip arms 104, 106 together toward the closed configuration so that the portion of target tissue to be clipped is gripped between the clip arms 104, 106. The clip arms 104, 106 may be moved between the open and closed configurations until the desired portion of tissue has been successfully gripped. Once the portion of the tissue to be clipped has been positioned between the clip arms 104, 106 as desired, the clip arms 104, 106 are moved toward the closed configuration so that the tissue is gripped therebetween. The clip arms 104, 106 are then moved further proximally into the capsule by the control member (not shown) so that the target tissue is firmly gripped between the clip arms 104, 106 which are held in the closed configuration by the capsule and the clip may then be deployed locking the clip arms 104, 106 in the closed configuration with the target tissue gripped therebetween and separating the capsule 108 from the proximal portion 110 of the device, deploying the clip in the body.

The above-described deployment process is one example of how the distal portion 102 of the device 100 may be deployed. The distal portion 102 may be deployed in a variety of different ways, depending on the configuration of the clip arms 104, 106 and the capsule 108, so long as deployment releases the capsule 108 from a proximal portion 110 of the device while also locking the clip arms 104, 106 in the closed configuration.

The devices 100', 200, 300, 400, 500, 500', 600 and 700 may be used in a manner substantially similar to the device 100. In particular, the clip arms 104', 106', 204, 206, 304, 306, 404, 406, 504, 506, 504', 506', 604, 606, 704 and 706 may be used to clip tissue as described above.

It will be appreciated by those skilled in the art that changes may be made to the embodiments described above without departing from the inventive concept thereof. It should be further appreciated that structural features and method associated with one of the embodiments can be incorporated into other embodiments. It is understood, therefore, that this invention is not limited to the particular embodiments discloses, but rather modifications are also covered within the scope of the present invention as defined by the appended claims.

What is claimed is:

1. A device for treating a tissue, comprising:

a capsule extending longitudinally from a proximal end to a distal end and including a channel extending therethrough;

clip arms, proximal ends of which are slidably received within the channel of the capsule so that the clip arms are movable between an open configuration, in which distal ends of the clip arms extend distally past the distal end of the capsule to be separated from one another, and a closed configuration, in which the clip arms are restrained via an interior surface of the capsule so that distal ends of the clips arms are drawn toward one another; and a reinforcement element coupled to the clip arms, the reinforcement element preventing deflection of the clip arms when engaging a target tissue;

wherein the reinforcement element is a suture, first and second end portions of the suture being fixed to an interior surface of each of the clip arms so a length of the suture extends between the clip arms; and further comprising a second suture including first and second ends coupled to a central member within the capsule channel, a medial portion of the second suture wrapping around a medial portion of the first suture.

2. The device of claim 1, wherein each of the clip arms include first and second holes extending therethrough, the first end portion of the suture extending through the first and second holes of a first clip arm and the second end portion of the suture extending through the first and second holes of a second clip arm, first and second ends of the suture each including an increased diameter element having a diameter larger than a diameter of the first and second holes to prevent the suture from being pulled through the first and second holes, wherein the increased diameter elements are positioned at the interior surface of the clip anus.

3. The device of claim 1, wherein the clip arms include first and second winged flanges extending from lateral sides of the clip arms, the first and second winged flanges configured to be folded toward a longitudinal axis of the clip arms to an interior surface thereof to secure ends of the suture to the clip arms.

* * * * *